US009234195B2

(12) United States Patent
Zhu et al.

(10) Patent No.: US 9,234,195 B2
(45) Date of Patent: Jan. 12, 2016

(54) ENHANCED GENE EXPRESSION

(75) Inventors: James Zhu, Cupertino, CA (US);
Guoliang Yu, Hillsborough, CA (US)

(73) Assignee: APPLIED STEMCELL, INC., Menlo Park, CA (US)

( * ) Notice: Subject to any disclaimer, the term of this patent is extended or adjusted under 35 U.S.C. 154(b) by 0 days.

(21) Appl. No.: 13/989,410

(22) PCT Filed: Nov. 25, 2011

(86) PCT No.: PCT/US2011/062163
§ 371 (c)(1),
(2), (4) Date: May 23, 2013

(87) PCT Pub. No.: WO2012/071580
PCT Pub. Date: May 31, 2012

(65) Prior Publication Data
US 2013/0252830 A1    Sep. 26, 2013

Related U.S. Application Data

(60) Provisional application No. 61/417,272, filed on Nov. 25, 2010.

(51) Int. Cl.
| | |
|---|---|
| *C12N 15/00* | (2006.01) |
| *C12N 15/11* | (2006.01) |
| *C12N 15/85* | (2006.01) |
| *C12N 15/90* | (2006.01) |
| C12N 15/09 | (2006.01) |
| C12N 15/63 | (2006.01) |
| C12N 15/64 | (2006.01) |
| C12N 15/67 | (2006.01) |
| C12N 15/87 | (2006.01) |
| C12P 21/06 | (2006.01) |

(52) U.S. Cl.
CPC ............... *C12N 15/11* (2013.01); *C12N 15/85* (2013.01); *C12N 15/907* (2013.01)

(58) Field of Classification Search
None
See application file for complete search history.

(56) References Cited

U.S. PATENT DOCUMENTS

| | | | |
|---|---|---|---|
| 2005/0208021 A1* | 9/2005 | Calos | 424/93.2 |
| 2006/0128020 A1* | 6/2006 | Calos | 435/456 |
| 2010/0075401 A1 | 3/2010 | Chen et al. | |

FOREIGN PATENT DOCUMENTS

| | | |
|---|---|---|
| CN | 1946842 A | 4/2007 |
| CN | 101511994 A | 8/2009 |
| WO | 2007137267 A2 | 11/2007 |
| WO | 2009068645 A1 | 6/2009 |

OTHER PUBLICATIONS

Chalberg et al., "Integration Specificity of Phage ΦC31 Integrase in the Human Genome" 357 Journal of Molecular Biology 28-48 (2006).*
Gierman et al., "Domain-wide regulation of gene expression in the human genome" 17(9) Genome Research 1286-1295 (2007).*
Liu et al., "Φc31 integrase induces chromosomal abberations in primary human fibroblasts" 13 Gene Therapy 1188-1190 (2006).*
Thyagarajan et al., "Site-Specific Genomic Integration in Mammalian Cells Mediated by Phage ΦC21 Integrase" 21(12) Molecular and Cellular Biology 3926-3934 (2001).*
Versteeg et al., "The Human Transcriptome Map Revearls Extremes in Gene Density, Intron Length, GC Content and Repeat Pattern for Domains of Highly and Weakly Expressed Genes" 13(9) Genome Research 1998-2004 (2003).*
Keravala et al., "Site-Specific Chromosomal Integration Mediated by ΦC31 Integrase" 435 Methods in Molecular Biology 165- 173 (2008).*
Caron et al., "The human transcriptome map: clustering of highly expressed genes in chromosomal domains" Science. 291 (5507): 1289-1292 (Feb. 16 2001).
Groth et al., "Phage integrases: biology and applications" Journal of Molecular Biology. 335 (3): 667-678 (Jan. 16, 2004).
Jiao et al., "Retargeting of pre-set regions on chromosome for high gene expression in mammalian cells" Molecular Engineering of Biological and Chemical Systems, Dspace©MIT's Open Access Articles Collection, 2005.
Zhou et al., "Genome-wide identification of chromosomal regions of increased tumor expression by transcriptome analysis" Cancer Research. 63 (18): 5781-5784 (Sep. 2003).

* cited by examiner

*Primary Examiner* — Nancy J Leith
(74) *Attorney, Agent, or Firm* — Jun He Law Offices P.C.; James J. Zhu

(57) ABSTRACT

The present disclosure is directed to a novel, unexpected approach of expressing exogenous gene(s) at increased levels by predictably, optionally irreversibly, incorporating the gene(s) into a region of increased gene expression (RIDGE) on a chromosome of a host cell. This approach is accomplished by identification of RIDGE(s) and further by integration of integrase-specific sites (e.g., attP or attB) in the presence of or mediated by integrase. The approach renders a high level of gene expression; predictability of the location of the exogenous genes, elimination of genetic instability or unwanted phenotype; and reduction of time and cost in optimizing protein production in host cells, which will be every useful in the production of therapeutic, prophylactic, and diagnostic proteins.

9 Claims, 4 Drawing Sheets

| Site | Sequence | % identity to attP |
|---|---|---|
| wt attB SEQ ID No.:1 | GTGCCAGGGCGTGCCCTTGGGCTCCCCGGGCGCG | 44% |
| wt attP SEQ ID No.:2 | CCCCAACTGGGGTAACCTTTGAGTTCTCTCAGTTGGGGG | 100% |

Figure 4

ENHANCED GENE EXPRESSION

CROSS-REFERENCE TO RELATED APPLICATIONS

This application is a National Stage application of PCT Patent Application No. PCT/US2011/062163, filed on Nov. 25, 2011, which application claims priority to U.S. Provisional Patent Application No. 61/417,272, filed on Nov. 25, 2010, which applications are specifically incorporated by reference in their entirety.

FIELD OF THE INVENTION

The present disclosure relates to the field of gene expression.

BACKGROUND OF THE INVENTION

High level of gene expression in mammalian cells has always been a challenge to production of a large amount of proteins for diagnostic or therapeutic uses. A typical process for protein production involves with the steps of 1) transfecting a vector comprising a gene of interest into mammalian cells such that the vectors may randomly incorporate into sites of chromosomes of the cells through recombination and 2) screening and selecting cells expressing a high level of expression of the gene of interest. Random recombination renders protein production as an art in science, rather a predictable, repeatable scientific process. Additionally, the large amount of selection work is also a costly, burdensome, unpredictable process. Therefore, there is a great need in the art to incorporate genes of interest into predictable, specific sites on chromosomes and reach a high level of gene expression.

SUMMARY OF THE INVENTION

One aspect of the present disclosure relates to methods of producing protein at a high level comprising the steps of predictably placing an exogenous gene of interest into a region of increased gene expression (RIDGE) on a chromosome in a host cell and expressing the gene in the host cell.

In certain embodiments, the methods herein include steps of identifying a RIDGE on a chromosome in a host cell and introducing an anchor gene onto the RIDGE. The anchor gene can be a transgene of interest or an integrase-specific site. The anchor gene can be introduced onto the RIDGE via homologous recombination.

In certain embodiments, the methods herein include steps of, for example, identifying a RIDGE on a chromosome in a host cell and introducing a first integrase-specific site to the RIDGE. The method further comprise the steps of constructing a vector comprising a gene of interest and a second integrase-specific site and introducing the vector into the host cell in the presence of an integrase, wherein the gene is irreversibly incorporate into the chromosome and flanked by two integrase-resulting sites. In certain embodiments, the integrase-resulting sites are attL and attR.

Another aspect of the present disclosure relates to isolated nucleotides comprising the sequence of at least a gene of interest and the sequence of an integrase-specific site.

Another aspect of the present disclosure relates to a vector comprising at least a gene of interest and an integrase-specific site.

Another aspect of the present disclosure relates to a host cell comprising at least a gene of interest flanked by integrase-resulting sites (e.g., attL and attR).

Another aspect of the present disclosure relates to a host cell having a plurality of the same gene into a single RIDGE or a plurality of RIDGEs (e.g. a first RIDGE and a second RIDGE) respectively in a host cell.

Another aspect of the present disclosure relates to a host cell having a first gene and a second gene into a single RIDGE or a first gene in a first RIDGE and a second gene into a second RIDGE.

Another aspect of the present disclosure relates to method of producing proteins by expression a plurality of genes in the single host cell herein.

BRIEF DESCRIPTION OF THE FIGURES

FIG. 4. Examples of wide-typea ttB and attP sequences.

EMBODIMENTS OF THE INVENTION

Figure 1:
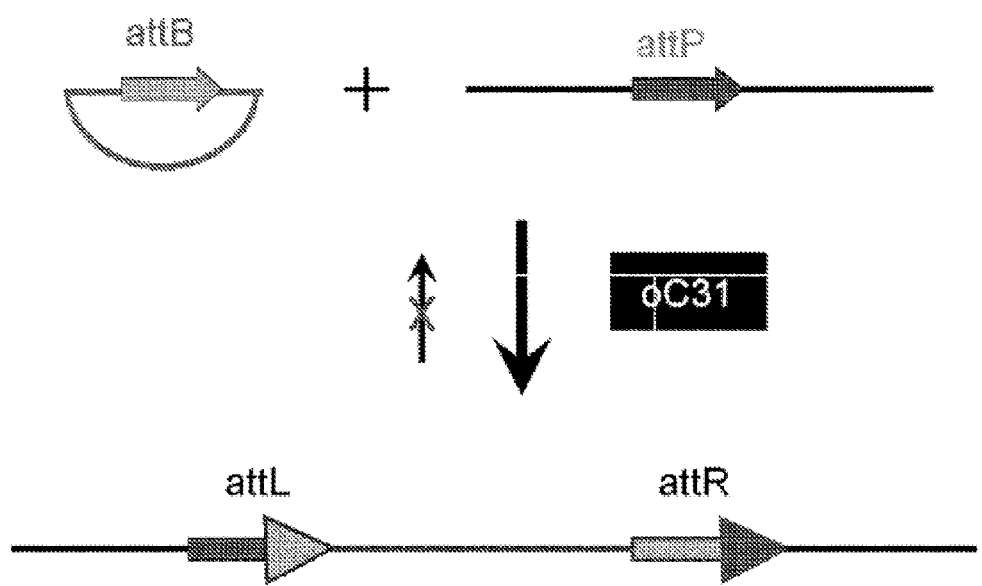
FIG. 1. A showing of how an integrase catalyzes irreversible recombination between attB and attP. For example, $\phi$C31 integrase is used to mediate integration of a plasmid bearing a first integrase-specific site (attP) into a chromosome containing a second integrase specific site (attB), resulting an irreversible integration of the vector into the chromosome and the vector is flanked by a set of integrase-resulting sites (attL and attR).

One aspect of the present disclosure is directed to a novel, unexpected approach to express genes of interest at an increased level by predictably, optionally irreversibly, incorporating the genes at specific gene integration site(s) onto a chromosome of a host cell. The present approach includes steps of, for example, identifying a specific gene integration site on a chromosome in a host cell; incorporating a first integrase-specific (e.g., attP or attB) to the site, constructing a vector comprising a gene of interest and a second integrase-specific (e.g., attB or attP) site; incorporating the vector into the host cell in the presence of or mediated by an integrase, wherein the gene is irreversibly incorporate into the chromosome and flanked by attL and attR.

I. Identification of Specific Gene Integration Site(s).

The term "specific gene integration site" used herein refers to a site or locus in a region of increased gene expression (RIDGE) on a chromosome. The RIDGE is a region on a chromosome which genes resides therein tend to be highly expressed. When an exogenous gene is introduced and incorporated onto a chromosome, the exogenous gene residing in a RIDGE tends to be expressed at a multiple folder higher (e.g., 2, 5, 10, 20, 50, 100, 200, 300, 500, 1000 folder higher) level than the same gene residing in a non-RIDGE or a randomly integrated site.

RIDGEs have been genome-wide identified through transcriptome mapping where clusters of highly expressed genes reside therein. Table I shows the RIDGEs that have been identified by comparative genomic hybridization in brain, breast, liver and lung tissue cells (See, Zhou et al., Can. Res. 63:5781-5784 (2003)). See also Caron et al., Science 291: 1289-1292 (2001).

tional targeting vectors can be engineered for insertion of transgenes at selected sites in the genome of interest where the vectors consist of a 5' homology arm (to the 3' of the site), followed by the transgene of interest (frequently preceded by

TABLE I (from Zhou et al., Can. Res. 63: 5781-5784 (2003) which is incorporated in its entirety by reference)

| CHR | Brain | Breast | Liver | Lung |
|---|---|---|---|---|
| 1 | 1p34, 1p36, 1q21, 1q31 | 1p34, 1p33, 1q21, 1q41, 1q42 | 1p34, 1q21, 1q42 | 1p33, 1p34, 1p36, 1q21, 1q42 |
| 2 | 2p23, 2p11, 2q35, 2q36, 2q37 | 2p21, 2p24, 2q11, 2q37 | 2p11, 2p25, 2q21, 2q35, 2q36 | 2p12, 2q11, 2q13, 2q21, 2q37 |
| 3 | 3p21, 3p22, 3q21, 3q28 | 3q25, 3q26, 3q29 | 3p21 | 3q21, 3q23, 3q27 |
| 4 | 4q13, 4q21, 4q34 | 4p16 | | 4p16 |
| 5 | | 5p15, 5q35 | | 5p15, 5q35 |
| 6 | 6p21, 6p24, 6q16 | 6p21 | 6p21 | 6p21 |
| 7 | 7p22, 7p12, 7p13, 7q22, 7q36 | 7q11, 7q22, 7q32, 7q34 | 7p13, 7p12 | 7p22, 7p13, 7p12, 7q11, 7q22 |
| 8 | 8p21, 8q24 | 8q24 | 8q24 | 8q24 |
| 9 | 9p21, 9q22, 9q34 | 9q32, 9q33 | 9p13, 9q34 | 9q22, 9q34 |
| 10 | 10q11, 10q22 | 10p15, 10q26 | 10q22, 10q24 | 10p15 |
| 11 | 11p15, 11q12, 11q13 | 11q13, 11q12 | 11q12, 11q13 | 11p15, 11p11, 11q12, 11q13 |
| 12 | 12p13, 12q13 | 12p11, 12q13, 12q24 | 12q13 | 12p13, 12p11, 12q13, 12q24 |
| 13 | | 13q14 | | |
| 14 | 14q32 | 14q32 | 14q11, 14q32 | 14q11, 14q32 |
| 15 | 15q14, 15q15 | 15q14, 15q22, 15q23, 15q24 | | 15q22, 15q24, 15q25, 15q26 |
| 16 | 16p13, 16p12, 16p11, 16q12, 16q24 | 16p13, 16p12, 16p11, 16q24 | 16p13, 16p12, 16p11, 16q22 | 16p13, 16p12, 16p11, 16q12, 16q22, 16q24 |
| 17 | 17q21, 17q23, 17q25 | 17p13, 17p11, 17q21, 17q23, 17q25 | 17p13, 17q12, 17q21, 17q25 | 17p11, 17q11, 17q21, 17q25 |
| 18 | | | | |
| 19 | 19p13, 19p12, 19q13 | 19p13, 19p12, 19p11, 19q13 | 19p13, 19q13 | 19p13, 19p12, 19q13 |
| 20 | 20p13, 20q11, 20q13 | 20q11, 20q13 | 20p13, 20q11 | 20p13, 20q11, 20q13 |
| 21 | 21q22 | 21q21 | | 21q22 |
| 22 | 22q12, 22q13 | 22q12, 22q13 | 22q13 | 22q11, 22q12 |
| X | Xp11, Xq11, Xq12, Xq13, Xq28 | Xp22, Xq12, Xq13, Xq22, Xq28 | | Xp11, Xq28 |

RIDGEs can also be identified through systems and methods as disclosed in Jiao et al. titled "retargeting of pre-set regions on chromosome for high gene expression in mammalian cells.". Briefly, a vector containing gfp2 reporter gene was transfected into mammalian cells (e.g., Chinese hamster ovary (CHO) cells) and the cells with highest expression level of GFP were selected where the linearized vector was integrated into the chromosome of the CHO cells and resided in a RIDGE. A gene of interest, for example, Interferon, was then used to replace gfp2 gene and the CHO cells with dimmest GFP fluorescence were selected with the ability of highly expressing interferon.

RIDGEs can also be identified by using the microarray analysis of whole cell or cytoplasm mRNA transcription level and identifies those of higher transcription (e.g., (e.g., 2, 5, 10, 20, 50, 100, 200, 300, 500, 1000 folder higher) than housekeeping mRNAs like beta-actin and identifying corresponding exon regions transcribing those RNA.

The specific gene integration site includes at least one of the following characteristics: 1) insertion of an exogenous gene should not disrupt the functions of regulatory elements or genes in the RIDGE or chromosome; 2) the site should be in an intergenic region; 3) the site should be spatially and temporally ubiquitous active; 4) the site should be transcriptional active at chromosomal level such that the transcription machinery is active at the site and a higher level of transcription; and 5) insertion of the exogenous gene should not interference the viability of the host cell.

The specific gene integration site contains nucleotide sequences known in the art. For example, DNA marker sequences of the RIDGEs in Table I are well known and readily accessible through gene data bank.

In certain embodiment, once the RIDGEs and specific gene integration sites are identified, transgenes can be incorporated into the site through recombination. For example, convena particular promoter or promoter-less), a positive selection marker gene-containing cassette, and a 3' homology arm (to the 5' of the site). The selection marker gene-containing cassette used in these methods consists of a ubiquitously expressed promoter such as the phosphoglycerate kinase promoter which drives the expression of a positive drug selection gene such as neomycin phosphotransferase or other suitable drug selection gene familiar in the art, followed by a polyadenylation signal sequence to confer efficient polyadenylation of the transcribed message. The selection cassette confers drug resistance when the vector integrates at the desired specific gene integration site via homologous recombination. The transcription or expression levels of transgenes are then analyzed.

In certain embodiment, integrase-specific sites are incorporated into the RIDGEs and specific gene integration sites via homologous recombination such that cells embodying the integrase-specific site(s) can be used as mater cell lines for incorporating different genes of interest when desired.

II. Incorporation of at Least a First Integrase-Specific Site to at Least a Specific Gene Integration Site The term "integrase-specific site" or "ISS" used herein means attP or attB. When a first ISS is attP, a corresponding second ISS is attB (or the first ISS is attB and the second ISS is attP) such that the first ISS and the second ISS can undergo site specific integration mediated by or in presence of an integrase.

In certain embodiments, RIDGEs are identified in accordance with the disclosed methods in Jiao et al. titled "retargeting of pre-set regions on chromosome for high gene expression in mammalian cells." and the report gene gfp2 was incorporated into a RIDGE in the CHO cells.

Figure 2:
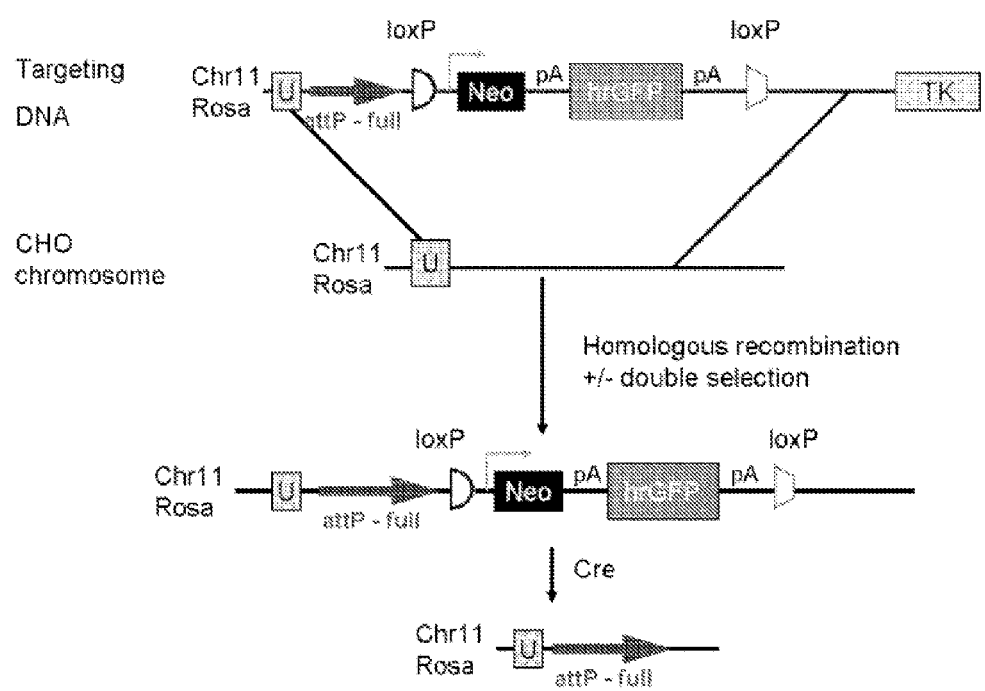
FIG. 2. A showing of how an attP site can be created in a RIDGE region of a chromosome. The RIDGE region is screened or identified by random integration of a reporter cassette the GFP (Green Fluorescence Protein) and NEO (Neomycine resistant) genes flanked by two LoxP sites. 5' to the cassette site contains an integrase (e.g., PhiC31 integrase) recognition site, attP, which will be integrated simultaneously with the cassette. The Cre/LoxP system is then used to remove the reporter cassette out of the RIDGE region and results in am attP site at the region.

As shown in FIG. 2, the gene sequence of gfp2 (or a fraction thereof), namely "U", can be used as a base for homologous recombination. A vector comprising the sequence of "U" as well as attP and double selection genes (e.g., Neo or hrGFP) flanked by loxP is introduced to the CHO cells and attP was incorporated adjacent to "U" along with Neo-hrGFP. The Neo & hRGFP can be reversibly removed by Cre enzyme. As a result, full attP is incorporated adjacently to the specific gene integration site and in the RIDGE.

In certain embodiments, RIDGEs have been genome-wide identified through methods disclosed by Zhou et al., Can. Res. 63:5781-5784 (2003). A specific DNA marker sequence in, for example, Chromosome II 11q13, known in the art, is used as an anchor sequence "U" as shown in FIG. 2.

In certain embodiments, Chromosome 11 ROSA 26 locus has been identified as a transcription active locus which is accessible to the transcription machinery and RNAs resulting from the transcription can be found inside cells (See U.S. Pat. No. 7,473,557). Sequences downstream of exon 1 of the ROSA26 locus can be used as an anchor sequence "U" as shown in FIG. 2.

In certain embodiments, there are a plurality "U"s or a plurality of specific gene integration sites (each with same or different sequences) along a chromosome or in different chromosomes so as to render a plurality of integrase-specific sites incorporated into a chromosome or chromosomes.

Figure 3:
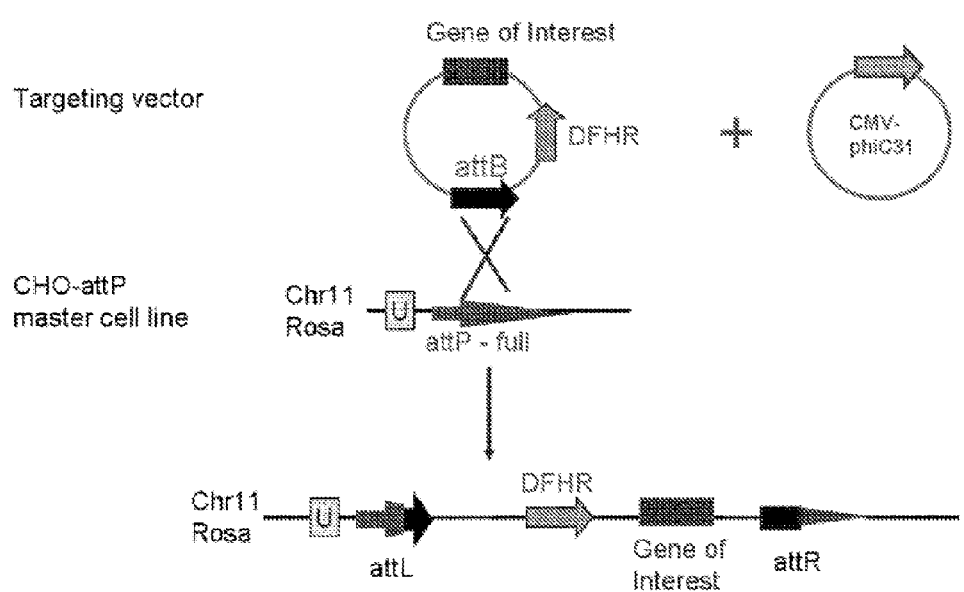
FIG. 3. A showing of how a vector comprising a gene of interest (e.g., a gene expressing an antibody or antigen-binding fragments thereof) and an attB site can be incorporated onto a chromosome in the presence of an integrase.

III. Construction of a Vector Comprising at Least a Gene of Interest and a Second Integrase-Specific Site As known in the art, a vector comprising at least a gene of interest and a second integrase-specific site can be readily constructed. The second intergrase-specific site is a corresponding site to the first ISS where the first and second will engage in a site specific integration in the presence of an integrase (See FIG. 1). As shown in FIG. 3, a targeting vector is constructed to contain a gene of interest, an attB site, and a market gene DHFR.

The gene of interest can be a gene encoding a protein of interest for therapeutic, diagnostic, or prophylactic purposes. For example, a protein of interest can be any one or more of the following antigens including but not limited to:

leukocyte markers, such as CD2, CD3, CD4, CD5, CD6, CD7, CD8, CD11a,b,c, CD13, CD14, CD18, CD19, CD20, CD22, CD23, CD27 and its ligand, CD28 and its ligands B7.1, B7.2, B7.3, CD29 and its ligand, CD30 and its ligand, CD40 and its ligand gp39, CD44, CD45 and isoforms, CDw52 (Campath antigen), CD56, CD58, CD69, CD72, CTLA-4, LFA-1 and TCR;

histocompatibility antigens, such as MHC class I or II, the Lewis Y antigens, SLex, SLey, SLea, and SLeb;

integrins, such as VLA-1, VLA-2, VLA-3, VLA-4, VLA-5, VLA-6, and LFA-1;

adhesion molecules, such as Mac-1 and p150,95;

selectins, such as L-selectin, P-selectin, and E-selectin and their counterreceptors VCAM-1, ICAM-1, ICAM-2, and LFA-3;

interleukins, such as IL-1, IL-2, IL-3, IL-4, IL-5, IL-6, IL-7, IL-8, IL-10, IL-11, IL-12, IL-13, IL-14; and IL-15;

interleukin receptors, such as IL-1R, 1L-2R, IL-4R, IL-5R, IL-6R, IL-7R, IL-8R, IL-10R, IL-11R, IL-12R, IL-13R, IL-14R, and IL-15R;

chemokines, such as PF4, RANTES, MIP1.alpha., MCP1, NAP-2, Grou, Grog, and IL-8;

growth factors, such as TNFalpha, TGFbeta, TSH, VEGF/VPF, PTHrP, EGF family, FGF, PDGF family, endothelin, and gastrin releasing peptide (GRP);

growth factor receptors, such as TNFalphaR, RGFbetaR, TSHR, VEGFR/VPFR, FGFR, EGFR, PTHrPR, PDGFR family, EPO-R, GCSF-R and other hematopoietic receptors;

interferon receptors, such as IFN.alpha.R, IFN.beta.R, and IFN.gamma.R;

Igs and their receptors, such as IgE, FceRI, and FCeRII;

tumor antigens, such as her2-neu, mucin, CEA and endosialin;

allergens, such as house dust mite antigen, IoI p1 (grass) antigens, and urushiol;

viral proteins, such as CMV glycoproteins B, H, and gCII, HIV-1 envelope glycoproteins, RSV envelope glycoproteins, HSV envelope glycoproteins, EBV envelope glycoproteins, VZV envelope glycoproteins, HPV envelope glycoproteins, Hepatitis family surface antigens;

toxins, such as pseudomonas endotoxin and osteopontin/uropontin, snake venom, and bee venom;

blood factors, such as complement C3b, complement C5a, complement C5b-9, Rh factor, fibrinogen, fibrin, and myelin associated growth inhibitor;

enzymes, such as cholesterol ester transfer protein, membrane bound matrix metalloproteases, and glutamic acid decarboxylase (GAD); and miscellaneous antigens including ganglioside GD3, ganglioside GM2, LMP1, LMP2, eosinophil major basic protein, eosinophil cationic protein, PANCA, Amadori protein, Type IV collagen, glycated lipids, .gamma.-interferon, A7, P-glycoprotein and Fas (AFO-1) and oxidized-LDL.

In certain embodiments, the protein of interest can be antibodies or fragments thereof which bind to an antigen (non-limiting example of antigens are shown as above). The antibodies or fragments can be polyclonal, monoclonal, of animal origin (e.g., murine, rabbit, camel), of human origin (e.g., fully human), chimeric, humanized, variable regions, CDRs, ScFv, bispecific, diabody, or other forms of antibodies with antigen-binding capabilities.

In certain embodiment, the vector can contain a plurality of genes of interest. Vectors herein include palsmids which are capable of expressing DNA sequences contained therein, where such sequences are operably linked to other sequences capable of effecting their expression, i.e., promotor/operator sequences. A vector is given a functional definition: any DNA sequence which is capable of effecting expression of a specified DNA code disposed therein.

IV. Incorporation of a Vector Comprising at Least a Gene of Interest and an Integrase-Specific Site to a Chromosome Comprising at Least Another Integrase-Specific Site in Presence of or Mediated by an Integrase.

As shown in FIG. 3, the vector containing a gene of interest and attB is introduced to a host cell having a chromosome wherein an attP sited is integrated as disclosed above. In the presence of or mediated by an integrase (e.g., φC31 integrase) in the host cell, the attP is integrated with attB so as to integrate the gene of interest into the chromosome. As a result, the gene of interest is flanked by two integrase-resulting sites (attL and attR) and located in or adjacent to a specific gene integration site in the region of increased gene expression (RIDGE) on a chromosome in a host cell.

In certain embodiments, the integrase is a resolvase or invertase or a member of the serine recombinase family of site-specific recombinases. For example, the integrase is φC31 (gene ID: 2715866); R4 (gene ID: 1099373), an integrase from the *Streptomyces* phagesTP901-1 (gene ID: 921049 and 921048), an integrase from the lactococcal phage SpoIVCA (gene ID: 937799), a recombinase that excises a prophage-like element from the *Bacillus* genome during sporulation.

In certain embodiments, host cells herein are cells which are capable of being transformed by a vector. Host cells can be prokaryotic (e.g., bacteria) or eukaryotic (e.g., yeast, plant, mammalian cells like CHO cells).

In certain embodiments, an integrase is present in a host cell by introducing an integrase gene-containing vector (including promoters and other elements for expression) into the host cell so that integrase can expressed in the cell.

In certain embodiments, an integrase-specific site can be attB (SEQ ID NO. 1) or homologies of attB (e.g., 98%, 95%, 90%, 85%, 80% homologous to SEQ ID NO. 1) or attP (SEQ ID NO. 2) or homologies of attP (e.g., 98%, 95%, 90%, 85%, 80% homologous to SEQ ID NO. 2). FIG. 4 shows an example of wide-type attB and attP sequences.

In certain embodiments, an integrase-resulting site is the sequence resulting from the integration of two corresponding integrase-specific sites. For example, an integrase-resulting site is attL or attR. attL can have a nucleotide sequence of GTGCCAGGGCGTGCCCTTGAGTTCTCAGTTGGGGG (SEQ ID NO. 3) or a homology of thereof (e.g., 98%, 95%, 90%, 85%, 80% homologous to SEQ ID NO. 3). attR can have a nucleotide sequence of CCCCAACTGGGGTAAC-CTTTGGGCTCCCCGGGCGCG (SEQ ID NO. 4) or a homology thereof (e.g., 98%, 95%, 90%, 85%, 80% homologous to SEQ ID NO. 4).

In certain embodiments, a plurality of vectors comprising a plurality of genes can be integrated into a plurality of integrase-specific sites on a chromosome or a plurality of chromosomes in a single host cell.

In certain embodiments, a gene of interest is a gene expressing an antibody or a fragment thereof. After integration into the RIDGE on a chromosome, the expression level of the antibody is multiple fold (e.g., 2, 3, 4, 5, 10, 20, 50, 100) higher than the level of random integration. For example, the antibody expression level reaches 1 pg/cell/day, 2 pg/cell/day, 5 pg/cell/day, 10 pg/cell/day, 20 pg/cell/day, 50 pg/cell/day, or 100 pg/cell/day.

Advantages.

The present disclosure renders a great benefit to the protein production. The present approach renders a high level of gene expression by integrating exogenous genes into region(s) of increased gene expression (RIDGE) on a chromosome of a host cell and ensuring a robust gene expression. The approach disclosed herein provides predictability of the location of the exogenous genes, eliminates genetic instability or unwanted phenotype caused by multiple rounds of amplifications and screening; and reduces the time and cost in optimizing protein production in host cells, which will be every useful in the production of therapeutic, prophylactic, and diagnostic proteins. In addition, after a first integrase-specific site is introduced into a RIDGE in a host cell, the host cell can be used as a master cell line for expression of various genes of interest, since a gene of interest can be easily incorporated onto the first site by introducing the integrase-present host cell with a vector containing the gene of interest and a second integrase-specific site.

The invention claimed is:

1. An isolated host cell comprising
   an exogenous gene flanked by a first integrase-resulting site and a second integrase-resulting site; and
   a fraction of green fluorescent protein (GFP) gene sequence,
   wherein the exogenous gene and the fraction of GFP gene sequence are located at a region of increased gene expression (RIDGE) on a chromosome of the cell, and wherein the fraction of GFP gene sequence does not express GFP.

2. The isolated host cell of claim 1, wherein the first integrase-resulting site is attL.

3. The isolated host cell of claim 1, wherein the second integrase-resulting site is attR.

4. An isolated host cell comprising
   a first exogenous gene flanked by a set of first integrase-resulting sites;
   a second exogenous gene flanked by a set of second integrase-resulting sites; and
   a fraction of GFP gene sequence,
   wherein each of the first exogenous gene, the second exogenous gene and the fraction of GFP gene sequence is located at a RIDGE in the host cell, and wherein the fraction of GFP gene sequence does not express GFP.

5. The isolated host cell of claim 4, wherein the set of the first integrase-resulting sites is the same or not the same as the set of the second integrase-resulting sites.

6. The isolated host cell of claim 4, wherein the first and second exogenous genes are located at a single RIDGE.

7. The isolated host cell of claim 4, wherein the first exogenous gene is located at a first RIDGE and the second exogenous gene is located at a second RIDGE.

8. The isolated host cell of claim 7, wherein the first and second RIDGEs are in a single chromosome.

9. The isolated host cell of claim 7, wherein the first RIDGE is in a first chromosome and the second RIDGE is in a second chromosome.

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Lambda phage

<400> SEQUENCE: 1
gtgccagggc gtgcccttgg gctccccggg cgcg                               34

<210> SEQ ID NO 2
<211> LENGTH: 39
<212> TYPE: DNA
<213> ORGANISM: Lambda phage

<400> SEQUENCE: 2
ccccaactgg ggtaaccttt gagttctctc agttggggg                          39

<210> SEQ ID NO 3
<211> LENGTH: 35
<212> TYPE: DNA
<213> ORGANISM: Lambda phage

<400> SEQUENCE: 3
gtgccagggc gtgcccttga gttctcagtt ggggg                              35

<210> SEQ ID NO 4
<211> LENGTH: 36
<212> TYPE: DNA
<213> ORGANISM: Lambda phage

<400> SEQUENCE: 4
ccccaactgg ggtaaccttt gggctccccg ggcgcg                             36
```